US012797119B2

(12) United States Patent
Yang et al.

(10) Patent No.: US 12,797,119 B2
(45) Date of Patent: Nov. 17, 2026

(54) CRYOABLATION NEEDLE HAVING J-T DOUBLE-CHANNEL

(71) Applicant: ACCUTARGET MEDIPHARMA (SHANGHAI) CO., LTD., Shanghai (CN)

(72) Inventors: Chi Yang, Shanghai (CN); Zhaohua Chang, Shanghai (CN)

(73) Assignee: ACCUTARGET MEDIPHARMA (SHANGHAI) CO., LTD., Shanghai (CN)

( * ) Notice: Subject to any disclaimer, the term of this patent is extended or adjusted under 35 U.S.C. 154(b) by 229 days.

(21) Appl. No.: 18/709,500

(22) PCT Filed: Nov. 1, 2022

(86) PCT No.: PCT/CN2022/128870

§ 371 (c)(1),
(2) Date: May 11, 2024

(87) PCT Pub. No.: WO2023/083048

PCT Pub. Date: May 19, 2023

(65) Prior Publication Data

US 2025/0000563 A1 Jan. 2, 2025

(30) Foreign Application Priority Data

Nov. 11, 2021 (CN) ......................... 202111329742.5

(51) Int. Cl.
*A61B 18/02* (2006.01)
*A61B 18/00* (2006.01)

(52) U.S. Cl.
CPC .... *A61B 18/02* (2013.01); *A61B 2018/00577* (2013.01); *A61B 2018/0262* (2013.01); *A61B 2018/0293* (2013.01)

(58) Field of Classification Search
CPC ............ A61B 18/02; A61B 2018/0262; A61B 2018/0212
See application file for complete search history.

(56) References Cited

U.S. PATENT DOCUMENTS 3,536,075 A * 10/1970 Thomas, Jr. ........... A61B 18/02 606/23
4,146,030 A * 3/1979 Holroyd ................ A61B 18/02 606/26
2006/0079867 A1* 4/2006 Berzak .................. A61B 18/02 606/23

* cited by examiner

*Primary Examiner* — Joseph A Stoklosa
*Assistant Examiner* — William Mossbrook
(74) *Attorney, Agent, or Firm* — MUNCY, GEISSLER, OLDS & LOWE, P.C.

(57) ABSTRACT

The present invention discloses a cryoablation needle having dual J-T slots, including: a vacuum wall and a J-T slot, where the vacuum wall includes: a needle rod and an inner tube; the needle rod is provided with a needle tip at a distal end; the inner tube penetrates through the needle rod, and a cavity is formed between the inner tube and the needle rod; the J-T slots include: a first J-T slot and a second J-T slot, and the first J-T slot and the second J-T slot penetrate through the inner tube; a distal end of the first J-T slot is located in the target area; and a distal end of the second J-T slot is located in the vacuum insulation area.

6 Claims, 11 Drawing Sheets

CRYOABLATION NEEDLE HAVING J-T DOUBLE-CHANNEL

TECHNICAL FIELD

The present invention relates to the technical field of cryoablation, and in particular to a cryoablation needle having dual J-T slots.

BACKGROUND

Cryoablation is a treatment approach that uses low temperature to destroy diseased tissues, which is considered to be an efficient and minimally invasive method to treat malignant tumors. The cryoablation is easy to operate, has few complications, and can effectively relieve pain. At the same time, ice balls formed by ablation have clear boundaries and are easy to observe, and lesions near large blood vessels or important organs can be safely ablated. The cryoablation may also adopt a multi-needle freezing manner, so that a wider ablation range is achieved, which is suitable for large lesions and irregular lesions.

In the process of cell freezing, ice crystals are firstly formed outside cells, which causes the concentration of extracellular solute to increase, resulting in a hypertonic environment, and water in the cells enters the outside of the cells, resulting in intracellular dehydration. The cells that lose water become shrunk and cell membranes are deformed, resulting in a "solution damage" in a high-concentration toxic environment. At the same time, ice crystals formed in the cells directly damage organelles and the cell membranes, causing further necrosis, commonly known as an "intracellular ice damage". The intracellular ice damage directly damages cell structures, and therefore is more destructive to the cells. Generally, the lower a cooling rate of the cells, the greater the probability of the "solution damage", and the higher the cooling rate, the easier it is to induce the "intracellular ice damage". Therefore, the higher cooling rate is generally pursued in the process of tumor cryoablation, which can kill tumors more thoroughly and greatly save surgery time.

The development of the cryoablation has undergone three stages. The first stage is a liquid nitrogen conveying and refrigeration technology, which conveys liquid nitrogen at −196° C. to a needle tip of a cryoablation needle by a low driving pressure to achieve the purpose of cryoablation. Because a cold source of this technology completely relies on the liquid nitrogen, which is located in a main machine or liquid nitrogen barrel and has a long conveying distance from the needle tip, during the conveying process, only when a whole conveying pipeline reaches −196° C., temperature of the needle tip can reach −196° C. Therefore, the cooling rate of liquid nitrogen refrigeration is the lowest in the prior art. The second stage is a direct throttling refrigeration technology, which uses the principle of "Joule Thompson Effect" (J-T for short), and conveys ultra-high pressure gas at room temperature to the J-T slot (a capillary tube that produces the J-T effect) inside the cryoablation needle to directly throttle to produce low temperature. The cooling rate of this technology is relatively the highest in the prior art. However, structures such as the J-T slot and a finned tube inside the needle tip may consume a part of cold, thus prolonging cooling time. In addition, the ultra-high pressure gas used is not highly popularized and is expensive, resulting in difficulty in the promotion of this technology. The third stage is a pre-cooled throttling refrigeration technology, the principle of which is to pre-cool normal industrial gas that is at room temperature by a supporting main machine, and then convey pre-cooled normal industrial gas to the J-T slot inside the cryoablation needle to produce ablation temperature that is lower than preset temperature by throttling. This technology solves the problem that gas sources are expensive and scarce. Furthermore, this technology combines a throttling refrigeration technology, and thus the cooling rate thereof is obviously higher than that of the liquid nitrogen refrigeration technology, but is still lower than that of the direct throttling refrigeration technology.

SUMMARY

For problems existing in the prior art, the present invention provides a cryoablation needle having dual J-T slots, to solve the problem of low cooling rate in the prior art.

In order to resolve the above technical problem, the present invention is implemented through the following technical solutions:

The present invention provides a cryoablation needle having dual J-T slots, including: a vacuum wall and J-T slots, where the vacuum wall includes: a needle rod and an inner tube; the needle rod is provided with a needle tip at a distal end; the inner tube penetrates through the needle rod, and a cavity is formed between the inner tube and the needle rod, the cavity being capable of forming a vacuum;

in an axis direction of the vacuum wall, a first preset distance exists between a distal end of the inner tube and the distal end of the needle rod; the distal end of the inner tube is an end of the inner tube close to the needle tip;

the J-T slots includes: a first J-T slot and a second J-T slot; the first J-T slot and the second J-T slot penetrate through the inner tube;

in areas in which the vacuum wall is distributed in the axis direction of the vacuum wall, an area in which the cavity is located is a vacuum insulation area, and an area in which the first preset distance exists is a target area;

a distal end of the first J-T slot is located in the target area; the distal end of the first J-T slot is an end of the first J-T slot close to the needle tip;

a distal end of the second J-T slot is located in the vacuum insulation area; the distal end of the second J-T slot is an end of the second J-T slot close to the needle tip;

in the axis direction of the vacuum wall, a second preset distance exists between the distal end of the first J-T slot and the needle tip, and the second preset distance at least ensures that an ice ball formed by freezing is wrapped around the needle tip, that is, a refrigerant fluid returns from the inside of the target area and the inside of the vacuum insulation area after being sprayed from the first J-T slot, where the refrigerant fluid exchanges heat with substances outside the whole target area during the process of returning from the inside of the target area; and in the axis direction of the vacuum wall, a third preset distance exists between the distal end of the second J-T slot and a distal end of the vacuum insulation area, and the third preset distance at least ensures that a refrigerant directly returns from the inside of the vacuum insulation area after being sprayed from the second J-T slot. Only a relatively static refrigerant exists in the target area, which will not exchange heat with the substances outside the target area, that is, the refrigerant does not release any cold in the target area during a freezing process, the distal end of the vacuum insulation area being an end of the vacuum insulation area close to the needle tip.

Preferably, the cryoablation needle having the dual J-T slots further includes: a switching assembly, where the switching assembly is connected to the first J-T slot and the second J-T slot separately, and the switching assembly is configured to switch the refrigerant between the first J-T slot and the second J-T slot.

Preferably, the switching assembly includes: an adjusting cavity, a freezing channel, a pre-purging channel and a sealing piece, where the freezing channel and the pre-purging channel are in communication with the adjusting cavity separately;

the freezing channel is further in communication with the first J-T slot;

the pre-purging channel is further in communication the second J-T slot;

the adjusting cavity is further in communication with a refrigerant intake channel for introducing the refrigerant;

the sealing piece is arranged in the adjusting cavity, and the sealing piece at least includes: a first adjusting position and a second adjusting position in the adjusting cavity;

when the sealing piece is located at the first adjusting position, the sealing piece directly or indirectly separates the freezing channel from the refrigerant intake channel; and when the sealing piece is located at the second adjusting position, the sealing piece directly or indirectly separates the pre-purging channel from the refrigerant intake channel.

Preferably, the sealing piece is a sealing ball.

Preferably, the cryoablation needle having the dual J-T slots further includes: a sealing piece adjusting apparatus, where the sealing piece adjusting apparatus is configured to adjust the sealing piece to be switched between the first adjusting position and the second adjusting position.

Preferably, the sealing piece adjusting apparatus includes a pull wire and a pull wire channel, where a distal end of the pull wire is connected to the sealing piece;

the pull wire penetrates through the pull wire channel; and the pull wire is capable of being controlled to move along the pull wire channel, to drive the sealing piece to be switched between the first adjusting position and the second adjusting position.

Preferably, the cryoablation needle having the dual J-T slots further includes: a guiding piece, where the guiding piece is connected to a proximal end of the pull wire; and the guiding piece is capable of being controlled to drive the pull wire to move along the pull wire channel, to drive the sealing piece to be switched between the first adjusting position and the second adjusting position.

Preferably, the cryoablation needle having the dual J-T slots further includes: a spring and a clamping piece, where one end of the spring is capable of moving synchronously with the distal end of the pull wire, and is further connected to the clamping piece; the clamping piece is capable of entering and exiting from a clamped position;

the other end of the spring is fixed relative to the vacuum wall;

when the clamping piece is located at the clamped position, the spring is limited by the clamping piece to keep in a deformation state, and the sealing piece is located at the first adjusting position;

the deformation state is a compression state or a tension state; and when the clamping piece exits from the clamped position, the spring is capable of generating a restoring force for restoring from the deformation state to a natural state, and the restoring force is capable of driving the pull wire to move, and then driving the sealing piece to enter the second adjusting position from the first adjusting position.

Preferably, the cryoablation needle having the dual J-T slots further includes: a spring stop, where a position of the spring stop is fixed relative to the vacuum wall; and an end of the spring fixed relative to the vacuum wall is connected to the spring stop.

Preferably, the cryoablation needle having the dual J-T slots includes: a first refrigerant intake channel, a second refrigerant intake channel, a freezing valve and a pre-purging valve, where the first refrigerant intake channel is connected to the first J-T slot;

the second refrigerant intake channel is connected to the second J-T slot;

the freezing valve is arranged on the first refrigerant intake channel; and the pre-purging valve is arranged on the second refrigerant intake channel.

Compared with the prior art, the present invention has the following advantages:

(1) According to the cryoablation needle having the dual J-T slots provided in the present invention, the refrigerant fluid is introduced into the second J-T slot to start freezing, so that all conveying pipelines at a main machine side and a cryoablation needle side can be pre-purged (cooled), and no cold is consumed at the target area during a pre-purging process. Therefore, all cold is used for cooling the conveying pipelines, and thus the rate of this conveying pipeline cooling process is the highest. Furthermore, no cold is released at the target area during the pre-purging process, so that there are no frosting and freezing phenomena in the target area, and then formal surgery can be performed directly.

(2) According to the cryoablation needle having the dual J-T slots provided in the present invention, only the target area of the vacuum wall of the pre-purged cryoablation needle is not cooled. The refrigerant fluid is introduced into the first J-T slot to start freezing, and all heat loads only come from the target area and tumor tissues outside the target area. Therefore, the cooling rate of this freezing process can be greatly increased.

(3) According to the cryoablation needle having the dual J-T slots provided in the present invention, after a needling test procedure ends, a pre-purging mode can be kept enabled, the inside (the distal end of the J-T slot) of the vacuum insulation area is kept at the lowest temperature. Since the target area does not release any cold, operations such as puncturing, scanning and positioning can be performed, and then the cryoablation needle is adjusted to a freezing mode after the puncturing is in place. In this case, the inside of the target area is directly reduced from the room temperature to the lowest temperature instantly. Therefore, ultimate rapid cooling of the formal surgery can be achieved.

(4) The cryoablation needle having the dual J-T slots provided in the present invention is wide in application range, and can be applied to all existing cryoablation technologies: liquid nitrogen conveying and refrigeration technology, direct throttling refrigeration technology and pre-cooled throttling refrigeration technology. The cryoablation needle having the dual J-T slots is not only applicable to percutaneous cryoablation instruments, but also applicable to cryoablation instruments of natural orifice transluminal surgery.

Certainly, implementing any product of the present invention does not necessarily need to simultaneously achieve all the advantages described above.

BRIEF DESCRIPTION OF DRAWINGS

In order to explain the technical solutions in the embodiments of the present invention or in the prior art more clearly, the drawings used in the description of the embodiments or the prior art will be briefly introduced below. Obviously, the drawings in the following description are merely some embodiments of the present invention. For those of ordinary skill in the art, other drawings can be obtained based on these drawings without creative efforts.

DESCRIPTION OF REFERENCE SIGNS

Figure 1:
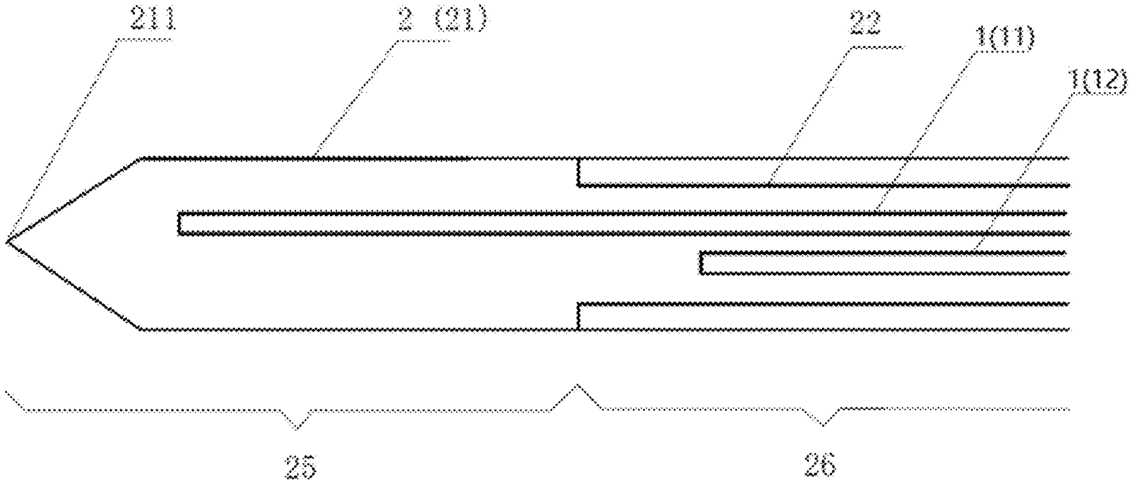
FIG. 1 is a diagram of a J-T slot adjustment principle of a hard cryoablation needle having dual J-T slots according to an embodiment of the present invention.

1—J-T slot,
11—first J-T slot,
12—second J-T slot,
2—vacuum wall,
21—needle rod,
211—needle tip,
22—inner tube,
221—inner tube front section,
222—inner tube rear section,
23—outer tube,
24—gasket,
25—target area,
26—vacuum insulation area,
27—spring stop,
28—vacuum tee,
281—tee connecting portion,
282—tee bypass,
291—vacuum connecting tube,
292—vacuum hose,
293—return gas connecting tube,
294—shunt,
3—mandrel,
31—mandrel thick section,
32—mandrel thin section,
4—finned tube,
5—sealing assembly,
51—sealing ring,
52—sealing slot,
53—sealing press piece,
6—gas intake tube,
7—gas return tube,
8—sliding block,
81—guiding tube,
82—sliding block positioning slot
83—middle fixing hole,
84—gas intake/return tube guiding hole,
9—handle,
91—handle positioning slot,
10—clamping piece,
101—hand-held portion,
102—positioning pin,
103—C-shaped ring,
120—spring,
13—outer sleeve,
15—switching assembly,
1511—freezing channel,
1512—adjusting cavity,
1513—pull wire channel,
152—pre-purging channel,
153—refrigerant intake channel,
16—sealing ball,
17—pull wire,
171—pull wire thick section,
172—pull wire thin section,
20—freezing valve, and
20'—pre-purging valve.

DETAILED DESCRIPTION

The technical solutions in embodiments of the present invention will be clearly and fully described in combination with the drawings of the embodiments of the present invention; it is obvious that the described embodiments are only a part of, and not all embodiments of, present invention. Based on the embodiments of the present invention, all other embodiments obtained by those of ordinary skill in the art without creative efforts should fall within the protection scope of the present invention.

In the description of the specification of the present invention, it should be understood that the term "upper portion", "lower portion", "upper end", "lower end", "upper surface", "lower surface" or the like indicates an orientation or positional relationship based on that shown in the drawings, which is merely for ease of description and simplicity of description, and is not intended to indicate or imply that the apparatus or element referred to must have a particular orientation, be constructed and operate in a particular orientation, and therefore cannot be construed as a limitation on the present invention.

In the description of the specification of the present invention, the terms "first" and "second" are used for descriptive purposes only, and cannot be construed as indicating or implying relative importance or implicitly indicating the number of technical features indicated. Therefore, a feature defined with "first" and "second" may explicitly or implicitly include one or more of the features.

In the description of the present invention, "a plurality of" means multiple, such as two, three, four or the like, unless specifically defined otherwise.

The technical solutions of the present invention will be described in detail below by specific embodiments. The following several specific embodiments may be mutually combined, and same or similar concepts or processes may not be repeatedly described in some embodiments.

Figure 2:
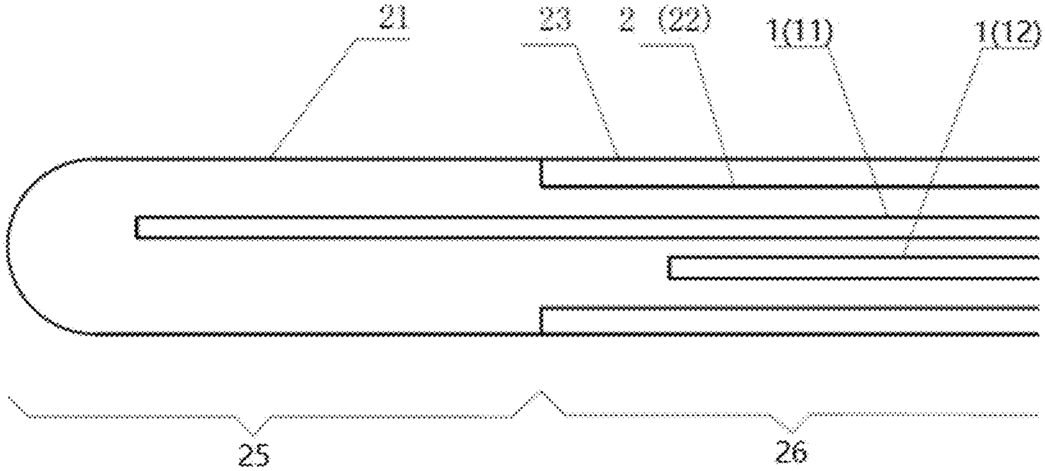
FIG. 2 is a diagram of a J-T slot adjustment principle of a flexible cryoablation needle having dual J-T slots according to an embodiment of the present invention.

As shown in FIG. 1 and FIG. 2, which each is a diagram of a J-T slot adjustment principle of a cryoablation needle having dual J-T slots according to an embodiment of the present invention.

Referring to FIG. 1 and FIG. 2, the cryoablation needle having the dual J-T slots according to this embodiment includes: a vacuum wall 2 and J-T slots 1.

The vacuum wall 2 includes: a needle rod 21 and an inner tube 22, and the needle rod 21 is provided with a needle tip 211 at a distal end. The inner tube 22 penetrates through the needle rod 21, and a cavity is formed between the inner tube 22 and the needle rod 21, the cavity being a cavity that can form a vacuum, which may be a permanent vacuum cavity or a real-time vacuum cavity. The vacuum cavity plays a role in heat insulation and preventing frostbite of normal tissues.

A first preset distance (the first preset distance can be understood as a spacing distance in an axis direction of the vacuum wall) exists between a distal end of the inner tube 22 and the distal end of the needle rod. The distal end of the inner tube 22 is an end of inner tube 22 close to the needle tip 211. The J-T slot 1 penetrates through the inner tube 22.

In areas in which the vacuum wall is distributed in the axis direction of the vacuum wall, since the vacuum cavity plays a role in heat insulation, an area in which the cavity is located is a vacuum insulation area 26, and an area in which the first preset distance exists is a target area 25.

The J-T slots 1 include: a first J-T slot 11 and a second J-T slot 12. The first J-T slot 11 and the second J-T slot 12 penetrate through the inner tube 22.

A distal end of the first J-T slot 11 is located in the target area 25. The distal end of the first J-T slot 11 is an end of the first J-T slot 11 close to the needle tip 211. When a refrigerant is introduced into the first J-T slot 11, it can be understood as being in a freezing mode.

A distal end of the second J-T slot 12 is located in the vacuum insulation area 26. The distal end of the second J-T slot 12 is an end of the second J-T slot 12 close to the needle tip 211. When the refrigerant is introduced into the second J-T slot 12, it can be understood as being in a pre-purging mode.

In the axis direction of the vacuum wall, a second preset distance exists between the distal end of the first J-T slot 11 and the needle tip, and the second preset distance at least ensures that an ice ball formed by freezing is wrapped around the needle tip, that is, a refrigerant fluid returns from the inside of the target area and the inside of the vacuum insulation area after being sprayed from the first J-T slot, where the refrigerant fluid exchanges heat with substances outside the whole target area during the process of returning from the inside of the target area.

In the axis direction of the vacuum wall, a third preset distance exists between the distal end of the second J-T slot 12 and a distal end of the vacuum insulation area, and the third preset distance at least ensures that the refrigerant fluid directly returns from the inside of the vacuum insulation area after being sprayed from the second J-T slot. Only a relatively static refrigerant exists in the target area, which will not exchange heat with the substances outside the target area. That is, the refrigerant does not release any cold in the target area during a freezing process. The distal end of the vacuum insulation area is an end of the vacuum insulation area close to the needle tip.

The first preset distance, the second preset distance and the third preset distance may be understood as spacing distances in the axis direction of the vacuum wall 2. In addition, an axial direction mentioned later can be understood as the axis direction of the vacuum wall 2.

In an embodiment, the vacuum wall is a hard-material vacuum wall, which can be applied to percutaneous cryoablation instruments. As shown in FIG. 1, the needle tip 211 is in the form of a pinpoint.

In an embodiment, the vacuum wall is a flexible-material vacuum wall, which can be applied to natural orifice transluminal ablation instruments. As shown in FIG. 2, the needle tip 211 is in the form of a circular arc. Preferably, the needle rod 21 and the inner tube 22 may be made of flexible nonmetallic materials or freely bendable metallic materials, such as PTFE or PTFE braided tubes or stainless-steel bellows.

In an embodiment, a use process of the cryoablation needle having the dual J-T slots is as follows: before surgery, the cryoablation needle in the pre-purging mode is taken out to be mutually connected to a main machine. The needle rod 21 (at least the target area 25) of the cryoablation needle is inserted into physiological saline to start a needling test function. A rewarming operation is firstly performed during needling test. When temperature of the needle tip rises to a certain temperature value within a certain time, it proves that a rewarming function is normal. Then, a program automatically performs a freezing operation. When the temperature of the needle tip is reduced to a certain temperature value within a certain time, it proves that a freezing function is normal. In this case, the time the needle tip is kept at the lowest temperature can be properly prolonged for sufficient pre-purging, and then the needling test is automatically stopped. During the freezing operation, whether there is a frosting phenomenon in the vacuum insulation area 26 is observed. If there is no frosting phenomenon, it proves that a heat insulation function is normal. Whether there is air leakage in the needle tip immersed in the physiological saline is observed during the whole process. If there is no air leakage, it proves that gas tightness is normal. After the needling test, conveying pipelines of both the main machine and the cryoablation needle have been pre-purged (cooled). Then, the freezing function can be enabled (or a separately configured pre-purging function can be enabled) at first, and freezing at this stage can be carried out at a lower working pressure, or gas can be intermittently introduced, so that the temperature at the distal end of the J-T slot can be kept at the lowest temperature while gas consumption can be reduced.

Next, under the condition of keeping the freezing function enabled, percutaneous puncturing can be performed under the guidance of imaging, so that the needle tip can reach an expected tumor position. In this case, the J-T slot can be adjusted to move toward the distal end, and stop at the first adjusting position, to switch to the freezing mode. Since the whole conveying pipeline is already in a low temperature state, a cooling heat load of the cryoablation needle only exists in the target area 25 and tumor tissues outside the target area. Therefore, after switching to the freezing mode, the temperature of the distal end of the J-T slot can still be kept at the lowest temperature, and an outer wall of the target area 25 will be reduced from normal temperature to below −100° C. instantly. In this way, surgical time for ablating a tumor with the same size is shortened, or a larger ablation range (ice ball) is produced within the same time. In addition, due to more rapid cooling of the tumor tissues, the probability of intracellular ice damage of tumor cells is greatly increased, and then freezing damage of the tumor cells is more thorough and the ablation effect is better.

Figure 8:
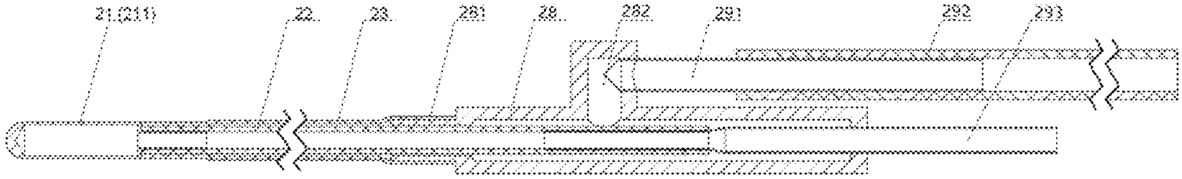
FIG. 8 is a schematic diagram of a vacuum wall of a flexible cryoablation needle having dual J-T slots according to a preferred embodiment of the present invention.

In a preferred embodiment, the vacuum wall of the flexible cryoablation needle may further include: a vacuum tee 28, a vacuum connecting tube 291, a vacuum hose 292 and a return gas connecting tube 293. Refer to FIG. 8. A proximal end of the inner tube 22 is connected to and sealed with a distal end of the return gas connecting tube 27. A proximal end of the outer tube 23 is connected to and sealed with a tee connecting portion 281. A proximal end of the vacuum tee 28 is connected to and sealed with the return gas connecting tube 27. A distal end of the vacuum connecting tube 291 is inserted into a tee bypass 282. The vacuum hose 292 is inserted into the vacuum connecting tube 291. By vacuum-pumping a proximal end of the vacuum hose 292, a gap between the inner tube 22 and the outer tube 23 can be kept in a vacuum state, to prevent frostbite of a normal natural cavity wall.

In a preferred embodiment, switching between the pre-purging mode and the freezing mode is realized by a switching assembly 15. The switching assembly 15 is connected to the first J-T slot and the second J-T slot separately. The switching assembly 15 is configured to switch the refrigerant between the first J-T slot and the second J-T slot.

In an embodiment, the switching assembly 15 includes: a freezing channel 1511, an adjusting cavity 1512, a pre-purging channel 152 and a sealing piece 16. The freezing channel 1511 and the pre-purging channel 152 are in communication with the adjusting cavity 1512 separately. The freezing channel 1511 is further in communication with the first J-T slot 11. The pre-purging channel 152 is further in communication with the second J-T slot 12. The adjusting cavity 1512 is further in communication with a refrigerant intake channel 153 for introducing the refrigerant.

The sealing piece 16 is arranged in the adjusting cavity 1512. The sealing piece 16 at least includes: a first adjusting position and a second adjusting position in the adjusting cavity 1512.

When the sealing piece 16 is located at the first adjusting position (a distal end of the adjusting cavity 1512), the sealing piece directly or indirectly separates the freezing channel 1511 from the refrigerant intake channel 153, as shown in FIG. 3, FIG. 4, FIG. 9 and FIG. 10. In this case, refrigerant gas introduced from a gas intake tube 6 can only enter the inside of the distal end of the vacuum insulation area 26 through the refrigerant intake channel 153, the adjusting cavity 1512, the pre-purging channel 152 and the second J-T slot 12, that is, in the pre-purging mode. In this case, return gas can be discharged from a gap between the second J-T slot 12 and the inner tube 22, a gap between the switching assembly 15 and the inner tube 22, and a gas return tube 7.

When the sealing piece 16 is located at the second adjusting position (a proximal end of the adjusting cavity 1512), the sealing piece 16 directly or indirectly separates the pre-purging channel 152 from the refrigerant intake channel 153, as shown in FIG. 6, FIG. 7, FIG. 12 and FIG. 13. In this case, the refrigerant gas introduced from the gas intake tube 6 can only enter the inside of a distal end of the target area 25 through the refrigerant intake channel 153, the adjusting cavity 1512, the freezing channel 1511 and the first J-T slot 11, that is, in the freezing mode. In this case, the return gas may have a same gas return path as that when the sealing piece is located at the first adjusting position.

In an embodiment, the adjusting cavity 1512 is arranged in the inner tube 22. A radial section of the adjusting cavity 1512 may be set to a flat shape, such as a straight slot, a rectangle, an ellipse, etc., so that a return gas space may exist between the adjusting cavity 1512 and the inner tube 22 (a circular cross section).

In a preferred embodiment, the sealing piece 16 is a sealing ball.

In a preferred embodiment, the cryoablation needle having the dual J-T slots further includes: a sealing piece adjusting apparatus, where the sealing piece adjusting apparatus is configured to adjust the sealing piece to be switched between the first adjusting position and the second adjusting position.

The sealing piece adjusting apparatus may include: a pull wire 17 and a pull wire channel 1513. A distal end of the pull wire 17 is connected to the sealing piece 16. The pull wire 17 penetrates through the pull wire channel 1513. The pull wire 17 can be controlled to move along the pull wire channel 1513, to drive the sealing piece 16 to be switched between the first adjusting position and second adjusting position.

In an embodiment, the cryoablation needle having the dual J-T slots further includes: a mandrel 3, where the mandrel 3 is arranged in the axis direction of the vacuum wall. The pull wire 17 is arranged in the mandrel 3. The cryoablation needle having the dual J-T slots further includes: a sealing assembly 5, where the sealing assembly 5 is configured to form a dynamic seal between the mandrel 3 and the pull wire 17.

In an embodiment, the sealing assembly 5 includes: a sealing ring 51, a sealing slot 52 and a sealing press piece 53. The sealing ring 51 is placed in the sealing slot 52. The sealing press piece 53 is screwed into the sealing slot 52 in the axial direction, to fix the sealing ring 51 between the sealing slot 52 and the sealing press piece 53. The mandrel 3 is inserted into the sealing ring 51 and the sealing press piece 53, so that the sealing ring 51 is radially extruded and deformed between the mandrel 3 and the sealing slot 52 to form a dynamic seal. Optionally, the sealing ring 51 may be a rubber sealing ring, such as a Buna-N rubber O-shaped ring, or may be a low-temperature-resistant Variceal sealing ring including fluoropolymer and a metal spring.

Figure 9:
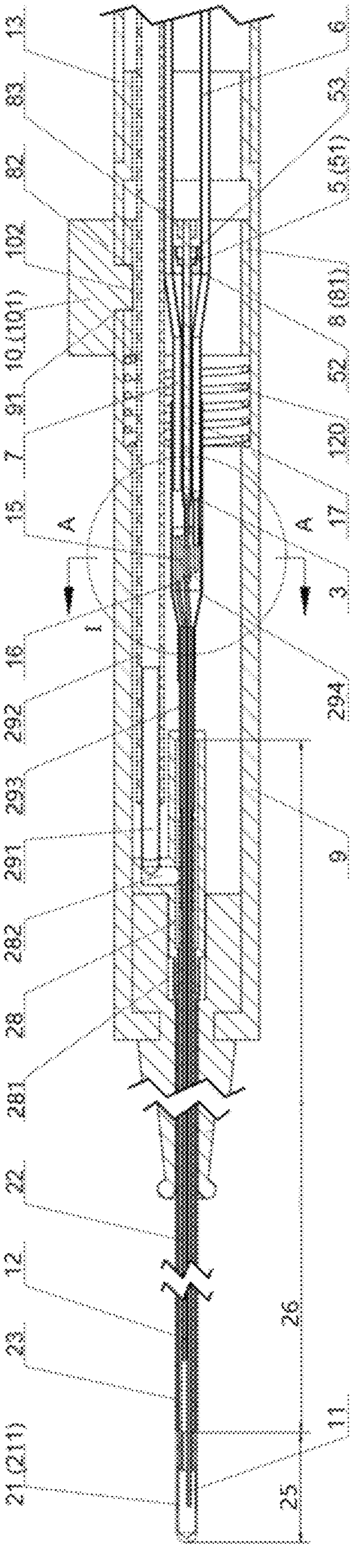
FIG. 9 is a diagram of a pre-purging mode of a flexible cryoablation needle having dual J-T slots according to a preferred embodiment of the present invention.
Figure 10:
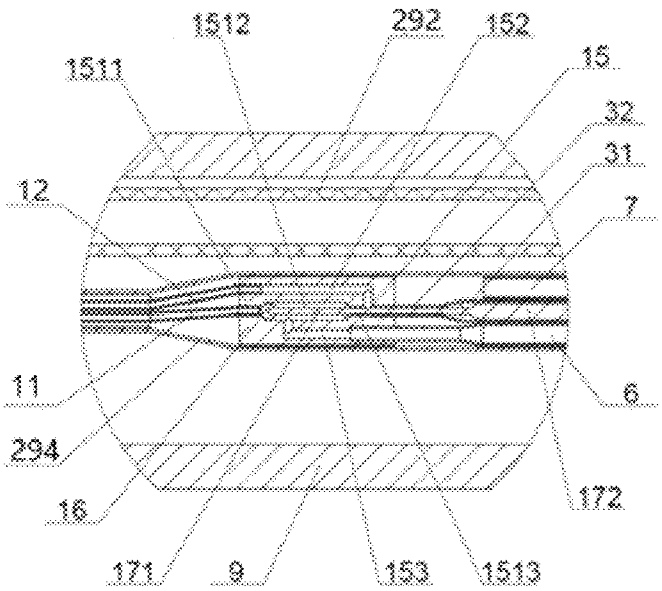
FIG. 10 is an enlarged view of a portion I in FIG. 9.
Figure 11:
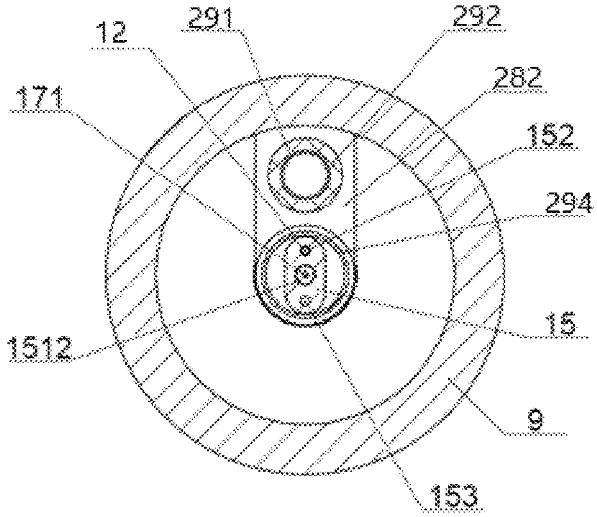
FIG. 11 is a cutaway view along an A-A direction in FIG. 9.
Figure 12:
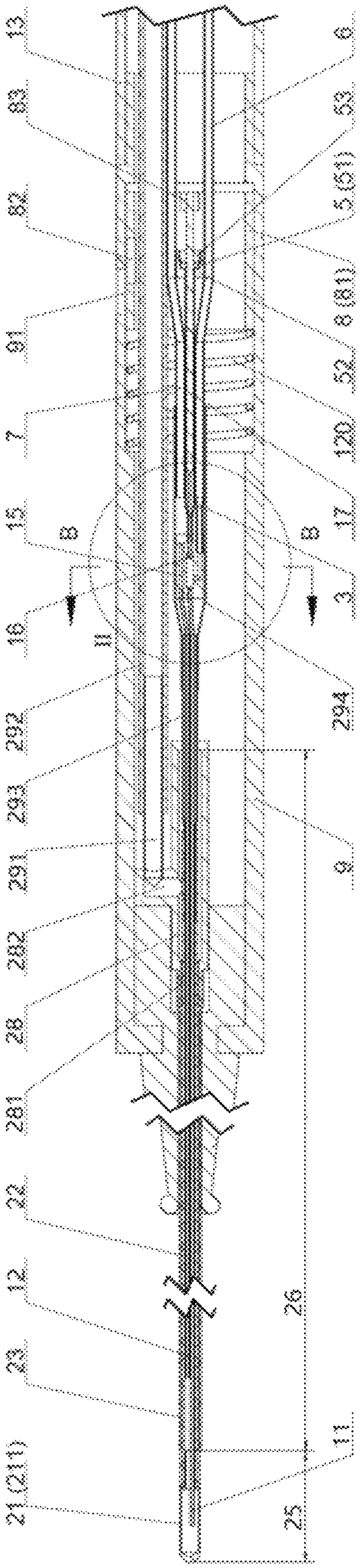
FIG. 12 is a diagram of a freezing mode of a flexible cryoablation needle having dual J-T slots according to a preferred embodiment of the present invention.
Figure 13:
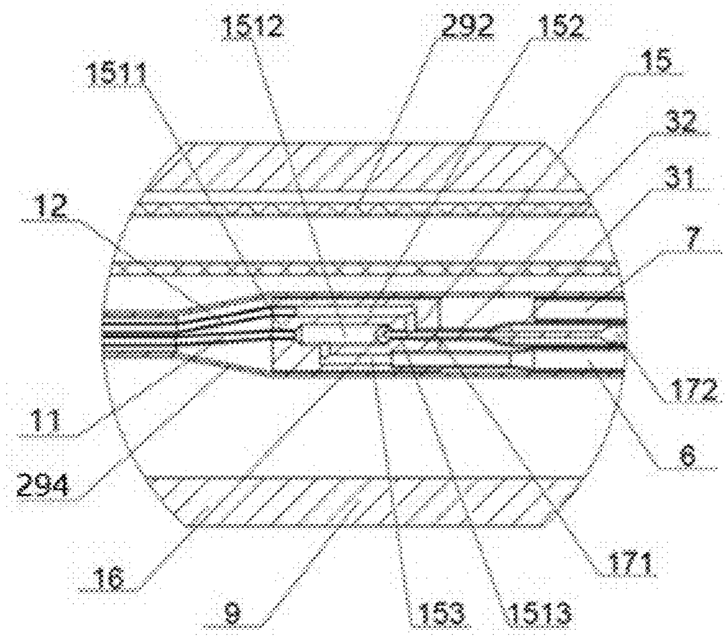
FIG. 13 is an enlarged view of a portion II in FIG. 12.
Figure 14:
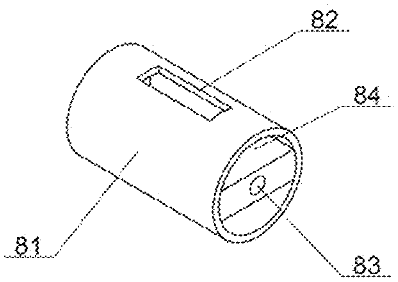
FIG. 14 is a schematic diagram of a sliding block according to a preferred embodiment of the present invention.

In an embodiment, the cryoablation needle having the dual J-T slots further includes: a shunt 294, configured to seal gaps between the gas intake tube 6, the gas return tube 7 and the mandrel 3. The gas intake tube 6, the gas return tube 7 and the mandrel 3 are inserted into a proximal end of the shunt 294 for sealing. Refer to FIG. 9 and FIG. 12.

In a preferred embodiment, the mandrel 3 includes: a mandrel thick section 31 and a mandrel thin section 32. The pull wire 17 includes: a pull wire thick section 171 and a pull wire thin section 172. The pull wire thin section 172 is arranged in the mandrel thin section 32. The pull wire thick section 171 is arranged in the mandrel thick section 131.

In a preferred embodiment, the cryoablation needle having the dual J-T slots further includes: a guiding piece, where the guiding piece is connected to a proximal end of the pull wire 17. The pull wire can be controlled to drive the pull wire to move along the pull wire channel, to drive the sealing piece to be switched between the first adjusting position and second adjusting position.

In an embodiment, the guiding piece is in the form of a sliding block. Refer to FIG. 3, FIG. 6, FIG. 9, FIG. 12 and FIG. 14. The sliding block 8 includes: a guiding tube 81. The guiding tube 81 is arranged in the axis direction of the vacuum wall. The guiding tube 81 is provided with a middle fixing hole 83. The distal end of the pull wire 3 is fixed to the middle fixing hole 83.

In an embodiment, the sliding block 8 further includes: a gas intake/return tube guiding hole 84 provided in the guiding tube 81. The gas intake tube 6 and the gas return tube 7 penetrate through the gas intake/return tube guiding hole 84.

Figure 3:
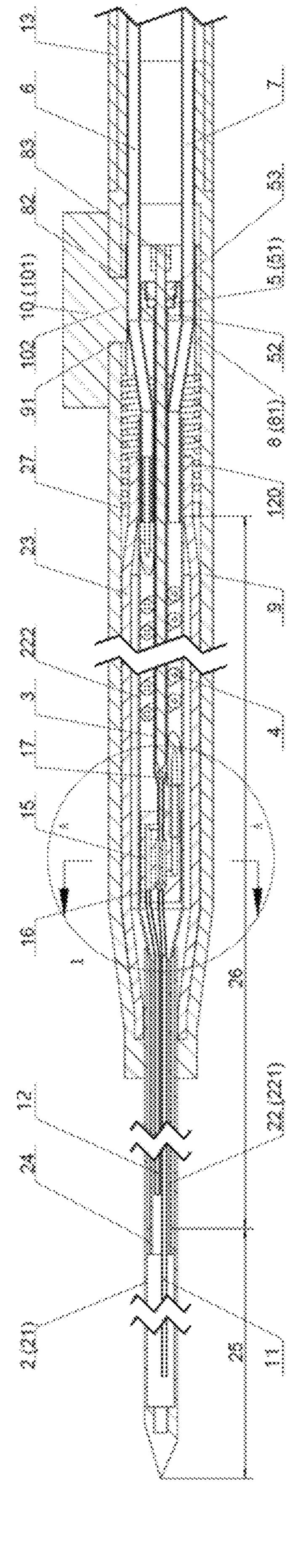
FIG. 3 is a diagram of a pre-purging mode of a hard cryoablation needle having dual J-T slots according to a preferred embodiment of the present invention.
Figure 4:
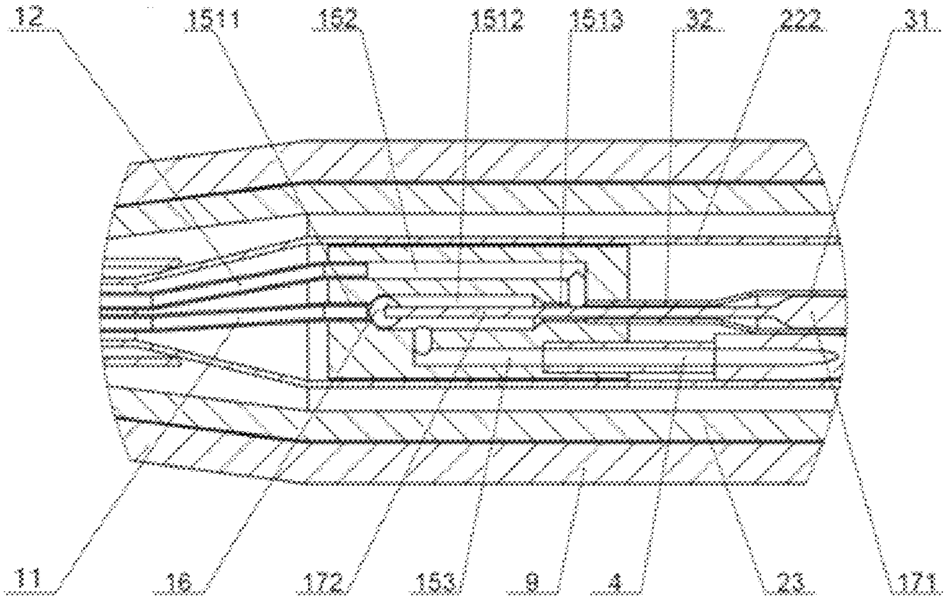
FIG. 4 is an enlarged view of a portion I in FIG. 3.
Figure 5:
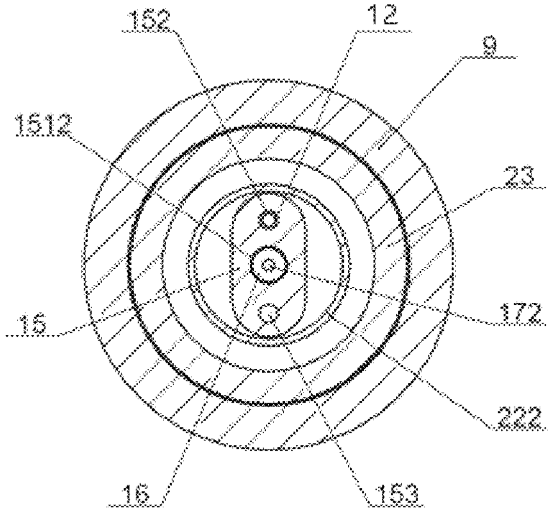
FIG. 5 is a cutaway view along an A-A direction in FIG. 3.
Figure 6:
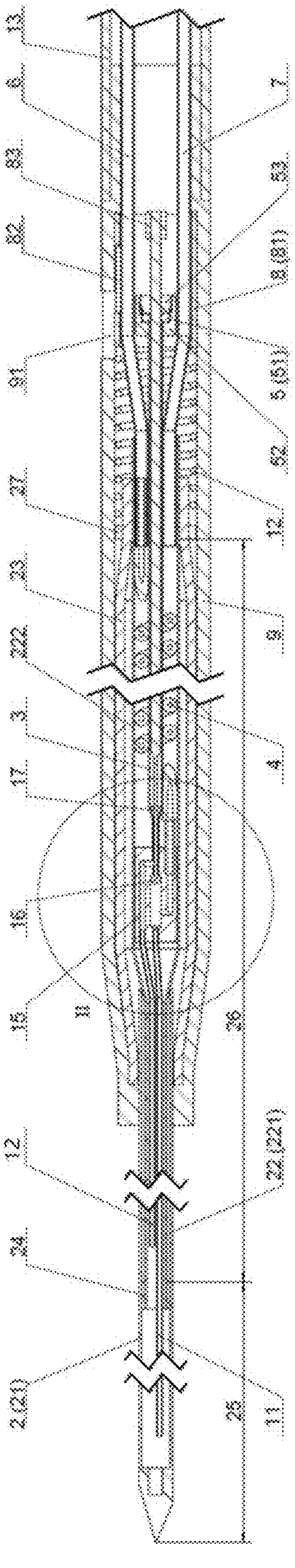
FIG. 6 is a diagram of a freezing mode of a hard cryoablation needle having dual J-T slots according to a preferred embodiment of the present invention.
Figure 7:
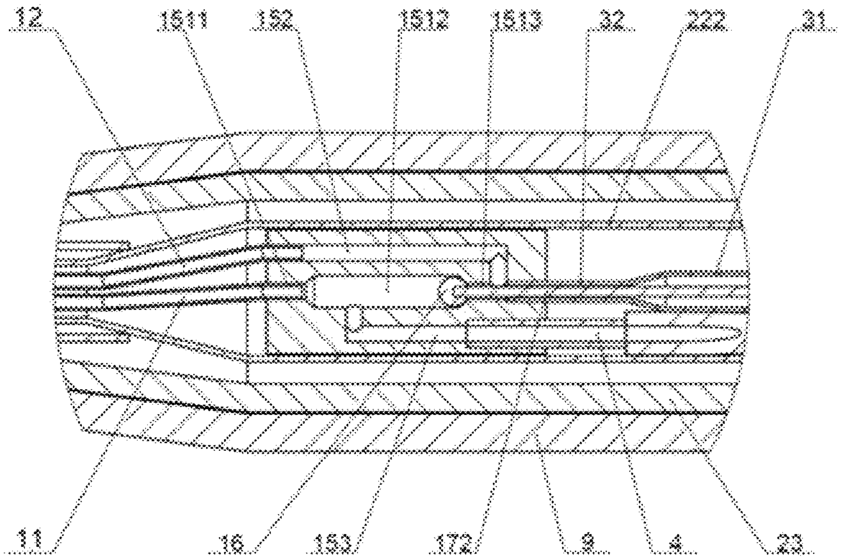
FIG. 7 is an enlarged view of a portion II in FIG. 6.

In an embodiment, position adjustment of the sealing piece may be achieved by manual forward and backward adjustment, or may be achieved by a prefabricated spring 120. The cryoablation needle having the dual J-T slots further includes: a clamping piece 10. One end of the spring 120 can move synchronously with the distal end of the pull wire 17, and is also connected to the clamping piece 10. The clamping piece 10 can enter and exit from a clamped position. The other end of the spring 120 is fixed relative to the vacuum wall. When the clamping piece 10 is located at the clamped position, the spring 120 is limited by the clamping piece 10 to keep in a deformation state, and the sealing piece 16 is located at the first adjusting position. Refer to FIG. 3 and FIG. 9. When the clamping piece 10 exits from the clamped position, the spring 120 can generate a restoring force for restoring from the deformation state to a natural state, and the restoring force can drive the pull wire 17 to move, and then drive the sealing piece 16 to enter the second adjusting position from the first adjusting position. In this embodiment, a position of a distal end of the spring 120 is fixed relative to the vacuum wall. A proximal end of the spring 120 is connected to the clamping piece 10. When the sealing piece 16 is located at the first adjusting position, the deformation state of the spring 120 is a compression state. When the clamping piece 10 exits from the clamped position, the restoring force (elastic force) of the spring 120 drives the pull wire to move, and then drives and the sealing piece 16 to enter the second adjusting position from the first adjusting position.

In a different embodiment, it can also be set that a position of the proximal end of the spring 120 is fixed relative to the vacuum wall. The proximal end of the spring 120 is connected to the clamping piece 10. When the clamping piece 10 is located at the clamped position, the spring 120 is limited by the clamping piece 10 to keep in a tension state, and the sealing piece 16 is located at the first adjusting position. When the clamping piece 10 exits from the clamped position, the restoring force (tensile force) of the spring 120 drives the pull wire 17 to move, and then drives the sealing piece 16 to enter the second adjusting position from the first adjusting position.

In a preferred embodiment, the cryoablation needle having the dual J-T slots further includes: a spring stop 27. A position of the spring stop 27 is fixed relative to the vacuum wall. Referring to FIG. 3 and FIG. 9, the distal end of the spring 120 is connected to the spring stop 27. The proximal end of the spring 120 is connected to the guiding tube 81 of the sliding block 8. The spring drives the sliding block, and then drives the pull wire to move.

In an embodiment, the clamping piece 10 includes: a positioning pin 102, as shown in FIG. 3 and FIG. 9. In this embodiment, the cryoablation needle having the dual J-T slots further includes a handle 9. The handle 9 is arranged at a proximal end of the cryoablation needle, which is convenient for grasping. The handle 9 is provided with a handle positioning slot 91. The sliding block 8 is provided with a sliding block positioning slot 82. When the distal end of the J-T slot is located at the first adjusting position, the positioning pin 102 is synchronously inserted into the handle positioning slot 91 and the sliding block positioning slot 82, so that a position of the sliding block 8 is fixed relative to the handle 9, that is, the current pre-purging mode is kept. In this embodiment, the spring 120 is in the compression state in this case. When it needs to be switched to the freezing mode, only the positioning pin 102 needs to be pulled out of the handle positioning slot 91 and the sliding block positioning slot 82.

Figure 15:
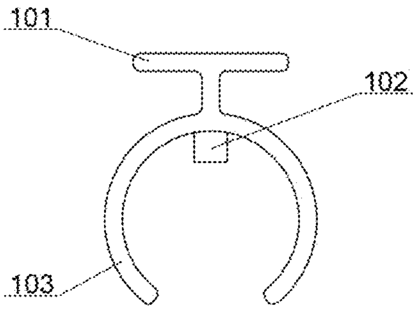
FIG. 15 is a schematic diagram of a clamping ring according to a preferred embodiment of the present invention.

In a preferred embodiment, in order to facilitate the fixing of the clamping piece and the insertion and removal adjustment of the clamping piece, the clamping piece 10 further includes: a hand-held portion 101 and a C-shaped ring 103. Refer to FIG. 15. The hand-held portion 101 and the positioning pin 102 are arranged on the C-shaped ring 103. The C-shaped ring 103 is wrapped around an outer wall of the handle 9, which can prevent the clamping piece from falling off radially.

In a different embodiment, when the handle 9 is not included, the C-shaped ring 103 only needs to be wrapped around an outer wall with a fixed position relative to the vacuum wall, which can also achieve the purpose of preventing the clamping piece from falling off radially.

In an embodiment, the vacuum wall 2 further includes: an outer tube 23. Refer to FIG. 3, FIG. 6, FIG. 9 and FIG. 12. A distal end of the outer tube 23 is hermetically connected to a proximal end of the needle rod 21, and a proximal end of the outer tube 23 is hermetically connected to the proximal end of the inner tube 22.

In a preferred embodiment, in order to increase the internal volume of the proximal end of the inner tube, for example, the finned tube 4 may be inserted into the proximal end of the inner tube, or more other components can be accommodated. Since the internal volume of the proximal end of the inner tube needs to be increased, the internal volume of the proximal end of the vacuum wall also needs to be increased. An outer diameter of the outer tube 23 is greater than an outer diameter of the needle rod 21. An inner diameter of the outer tube 23 is greater than an inner diameter of the needle rod 21. The distal end of the outer tube 23 is an end of the outer tube 23 close to the needle tip 211. The proximal end of the outer tube 23 is an end of the outer tube 23 far away from the needle tip 211. Furthermore, from the distal end to the proximal end of the inner tube 22, the inner tube 22 sequentially includes: an inner tube front section 221 and an inner tube rear section 222. An outer diameter of the inner tube rear section 222 is greater than an outer diameter of the inner tube front section 221. An inner diameter of the inner tube rear section 222 is greater than an inner diameter of the inner tube front section 221. The inner tube front section 221 is located inside the needle rod 21. The inner tube rear section 222 is located inside the outer tube 23. The adjusting cavity 1512 is arranged inside the inner tube rear section 222. Refer to FIG. 3, FIG. 6, FIG. 9 and FIG. 12.

In an embodiment, switching between the first J-T slot and the second J-T slot can also be achieved by two refrigerant intake channels. Specifically, the cryoablation needle having the dual J-T slots includes: a first refrigerant intake channel, a second refrigerant intake channel, a freezing valve 20 and a pre-purging valve 20'. The first refrigerant intake channel is connected to the first J-T slot 11. The second refrigerant intake channel is connected to the second J-T slot 12. The freezing valve 20 is arranged on the first refrigerant intake channel. The pre-purging valve 20' is arranged on the second refrigerant intake channel.

When the pre-purging valve 20' is opened, the refrigerant can be introduced into the second refrigerant intake channel, and the refrigerant can enter the distal end of the second J-T slot 12. In this case, it is in the pre-purging mode. When the freezing valve 20 is opened, the refrigerant can be introduced into the first refrigerant intake channel, and the refrigerant can enter the distal end of the first J-T slot 11. In this case, it is in the freezing mode.

In a preferred embodiment, the cryoablation needle having the dual J-T slots further includes: a mandrel 3, where the mandrel 3 is arranged in the axis direction of the vacuum wall.

In a preferred embodiment, in order to improve a heat dissipation function, the cryoablation needle having the dual J-T slots further includes: a finned tube 4, where the finned tube 4 is arranged on an outer wall of the mandrel 3.

Figure 16:
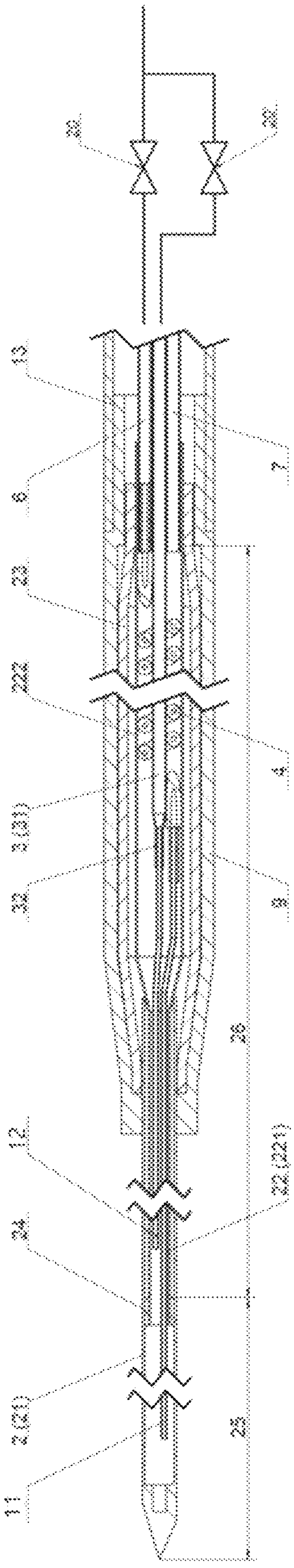
FIG. 16 is a schematic diagram of a hard cryoablation needle according to another preferred embodiment of the present invention.
Figure 17:
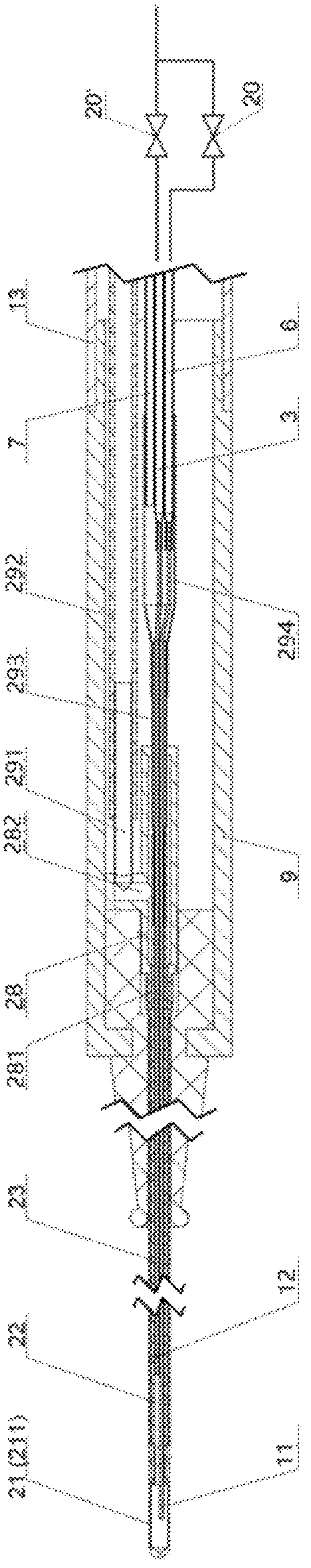
FIG. 17 is a schematic diagram of a flexible cryoablation needle according to another preferred embodiment of the present invention.

In an embodiment, the finned tube 4 can be used as the first refrigerant intake channel. One end of the finned tube 4 is connected to the first J-T slot, and the other end is connected to the gas intake tube 6. The freezing valve is arranged on the gas intake tube 6. The mandrel 3 can be used as the second refrigerant intake channel, and is connected to the second J-T slot. The pre-purging valve 20' is arranged on the mandrel 3. Refer to FIG. 16 and FIG. 17.

In a different embodiment, the mandrel 3 can also be used as the first refrigerant intake channel, and is connected to the first J-T slot. The finned tube 4 can also be used as the second refrigerant intake channel, and is connected to second J-T slot.

In an embodiment, in order to wrap around components such as the gas intake tube and the gas return tube, and make the cryoablation needle cleaner in appearance and more convenient in operation, an outer sleeve 13 is further arranged on the outer wall of the handle 9. Refer to FIG. 3, FIG. 6, FIG. 9 and FIG. 12.

In a preferred embodiment, the pre-purging mode, that is, the refrigerant fluid being introduced into the second J-T slot, can be set to a factory delivery state of the product, and an operator can directly complete the pre-purging of the product through a needling test procedure. After needling test/pre-purging is completed, the product is further adjusted to the freezing mode, that is, the refrigerant fluid being introduced into the first J-T slot. After freezing is enabled, since the cryoablation needle is pre-purged, the target area 25 will rapidly cool down to the lowest temperature.

In the description of this specification, description of reference terms such as "an implementation", "an embodiment", "a specific implementation process" or "an example" means including specific features, structures, materials, or characteristics described in the embodiment or example in at least one embodiment or example of the present invention. In this specification, exemplary descriptions of the foregoing terms do not necessarily refer to the same embodiment or example. Furthermore, specific features, structures, materials or characteristics described may be combined in any suitable manner in one or more embodiments or examples.

Finally, it should be noted that the foregoing embodiments are merely intended for describing the technical solutions of the present invention, but not for limiting the present invention. Although the present invention is described in detail with reference to the foregoing embodiments, persons of ordinary skill in the art should understand that they may still make modifications to the technical solutions described in the foregoing embodiments or make equivalent replacements to some or all technical features thereof, without making the essence of the corresponding technical solutions departing from the scope of the technical solutions of the embodiments of the present invention.

The invention claimed is:

1. A cryoablation needle having dual Joule Thompson (J-T) J T slots, comprising:

a vacuum wall;

J-T slots;

a switching assembly;

a sealing piece adjusting apparatus;

a spring; and a clamping piece, wherein the vacuum wall comprises:

a needle rod, the needle rod being provided with a needle tip at a distal end; and an inner tube, wherein the inner tube penetrates through the needle rod, and a cavity is formed between the inner tube and the needle rod, the cavity being capable of forming a vacuum, wherein, in an axis direction of the vacuum wall, a first preset distance exists between a distal end of the inner tube and the distal end of the needle rod; the distal end of the inner tube is an end of the inner tube close to the needle tip, wherein the J-T slots comprise: a first J-T slot and a second J-T slot, wherein the first J-T slot and the second J-T slot penetrate through the inner tube, wherein in areas in which the vacuum wall is distributed in the axis direction of the vacuum wall, an area in which the cavity is located is a vacuum insulation area, and an area in which the first preset distance exists is a target area, wherein a distal end of the first J-T slot is located in the target area; the distal end of the first J-T slot is an end of the first J-T slot close to the needle tip;

wherein a distal end of the second J-T slot is located in the vacuum insulation area; the distal end of the second J-T slot is an end of the second J-T slot close to the needle tip, wherein a refrigerant is introduced into only one of the first J-T slot and the second J-T slot at a time, wherein in the axis direction of the vacuum wall, a second preset distance exists between the distal end of the first J-T slot and the needle tip, and the second preset distance at least ensures that an ice ball formed by freezing is wrapped around the needle tip, wherein in the axis direction of the vacuum wall, a third preset distance exists between the distal end of the second J-T slot and a distal end of the vacuum insulation area, and the third preset distance at least ensures that the refrigerant directly returns from the inside of the vacuum insulation area after being sprayed from the second J-T slot, the distal end of the vacuum insulation area being an end of the vacuum insulation area close to the needle tip, wherein the switching assembly is connected to the first J-T slot and the second J-T slot separately, and the switching assembly is configured to switch the refrigerant between the first J-T slot and the second J-T slot, wherein the switching assembly comprises:

an adjusting cavity;

a freezing channel;

a pre-purging channel; and a sealing piece, wherein the freezing channel and the pre-purging channel are in communication with the adjusting cavity separately, wherein the freezing channel is further in communication with the first J-T slot; the pre-purging channel is further in communication the second J-T slot, wherein the adjusting cavity is further in communication with a refrigerant intake channel for introducing the refrigerant, wherein the sealing piece is arranged in the adjusting cavity, and the sealing piece at least comprises: a first adjusting position and a second adjusting position in the adjusting cavity; when the sealing piece is located at the first adjusting position, the sealing piece directly or indirectly separates the freezing channel from the refrigerant intake channel, wherein, when the sealing piece is located at the second adjusting position, the sealing piece directly or indirectly separates the pre-purging channel from the refrigerant intake channel, wherein the sealing piece adjusting apparatus is configured to adjust the sealing piece to be switched between the first adjusting position and the second adjusting position, wherein the sealing piece adjusting apparatus comprises:

a pull wire; and a pull wire channel, wherein a distal end of the pull wire is connected to the sealing piece; the pull wire penetrates through the pull wire channel, wherein the pull wire is capable of being controlled to move along the pull wire channel, to drive the sealing piece to be switched between the first adjusting position and the second adjusting position, wherein one end of the spring is capable of moving synchronously with the distal end of the pull wire, and is further connected to the clamping piece; the clamping piece is capable of entering and exiting from a clamped position, wherein the other end of the spring is fixed relative to the vacuum wall, wherein, when the clamping piece is located at the clamped position, the spring is limited by the clamping piece to keep in a deformation state, and the sealing piece is located at the first adjusting position, wherein the deformation state is a compression state or a tension state, and wherein, when the clamping piece exits from the clamped position, the spring is capable of generating a restoring force for restoring from the deformation state to a natural state, and the restoring force is capable of driving the pull wire to move, and then driving the sealing piece to enter the second adjusting position from the first adjusting position.

2. The cryoablation needle having the dual J-T slots according to claim 1, wherein the sealing piece is a sealing ball.

3. The cryoablation needle having the dual J-T slots according to claim 1, further comprising a guiding piece, wherein the guiding piece is connected to a proximal end of the pull wire, and wherein the guiding piece is capable of being controlled to drive the pull wire to move along the pull wire channel, to drive the sealing piece to be switched between the first adjusting position and the second adjusting position.

4. The cryoablation needle having the dual J-T slots according to claim 1, further comprising a spring stop, wherein a position of the spring stop is fixed relative to the vacuum wall, and wherein an end of the spring fixed relative to the vacuum wall is connected to the spring stop.

5. The cryoablation needle having the dual J-T slots according to claim 1, comprising:

a first refrigerant intake channel;

a second refrigerant intake channel;

a freezing valve; and a pre-purging valve, wherein the first refrigerant intake channel is connected to the first J-T slot, and wherein the second refrigerant intake channel is connected to the second J-T slot; the freezing valve is arranged on the first refrigerant intake channel; and the pre-purging valve is arranged on the second refrigerant intake channel.

6. A cryoablation needle having the dual Joule Thompson (J-T) slots, comprising:

a vacuum wall;

J-T slots;

a switching assembly;

a sealing piece adjusting apparatus;

a guiding piece;

a spring; and a clamping piece, wherein the vacuum wall comprises:

a needle rod provided with a needle tip at a distal end; and an inner tube, wherein the inner tube penetrates through the needle rod, and a cavity is formed between the inner tube and the needle rod, the cavity being capable of forming a vacuum, wherein, in an axis direction of the vacuum wall, a first preset distance exists between a distal end of the inner tube and the distal end of the needle rod; the distal end of the inner tube is an end of the inner tube close to the needle tip, wherein the J-T slots comprise: a first J-T slot and a second J-T slot, wherein the first J-T slot and the second J-T slot penetrate through the inner tube, wherein, in areas in which the vacuum wall is distributed in the axis direction of the vacuum wall, an area in which the cavity is located is a vacuum insulation area, and an area in which the first preset distance exists is a target area, wherein a distal end of the first J-T slot is located in the target area; the distal end of the first J-T slot is an end of the first J-T slot close to the needle tip, wherein a distal end of the second J-T slot is located in the vacuum insulation area; the distal end of the second J-T slot is an end of the second J-T slot close to the needle tip, wherein a refrigerant is introduced into only one of the first J-T slot and the second J-T slot at a time, wherein, in the axis direction of the vacuum wall, a second preset distance exists between the distal end of the first J-T slot and the needle tip, and the second preset distance at least ensures that an ice ball formed by freezing is wrapped around the needle tip, wherein, in the axis direction of the vacuum wall, a third preset distance exists between the distal end of the second J-T slot and a distal end of the vacuum insulation area, and the third preset distance at least ensures that the refrigerant directly returns from the inside of the vacuum insulation area after being sprayed from the second J-T slot, the distal end of the vacuum insulation area being an end of the vacuum insulation area close to the needle tip, wherein one end of the spring is capable of moving synchronously with the distal end of the pull wire, and is further connected to the clamping piece; the clamping piece is capable of entering and exiting from a clamped position, wherein the other end of the spring is fixed relative to the vacuum wall, wherein, when the clamping piece is located at the clamped position, the spring is limited by the clamping piece to keep in a deformation state, and the sealing piece is located at the first adjusting position, wherein the deformation state is a compression state or a tension state, wherein, when the clamping piece exits from the clamped position, the spring is capable of generating a restoring force for restoring from the deformation state to a natural state, and the restoring force is capable of driving the pull wire to move, and then driving the sealing piece to enter the second adjusting position from the first adjusting position, wherein the switching assembly is connected to the first J-T slot and the second J-T slot separately, and the switching assembly is configured to switch the refrigerant between the first J-T slot and the second J-T slot, wherein the switching assembly comprises:

an adjusting cavity;

a freezing channel;

a pre-purging channel; and a sealing piece, wherein the freezing channel and the pre-purging channel are in communication with the adjusting cavity separately, wherein the freezing channel is further in communication with the first J-T slot; the pre-purging channel is further in communication the second J-T slot, wherein the adjusting cavity is further in communication with a refrigerant intake channel for introducing the refrigerant, wherein the sealing piece is arranged in the adjusting cavity, and the sealing piece at least comprises: a first adjusting position and a second adjusting position in the adjusting cavity; when the sealing piece is located at the first adjusting position, the sealing piece directly or indirectly separates the freezing channel from the refrigerant intake channel, wherein, when the sealing piece is located at the second adjusting position, the sealing piece directly or indirectly separates the pre-purging channel from the refrigerant intake channel, wherein the sealing piece adjusting apparatus is configured to adjust the sealing piece to be switched between the first adjusting position and the second adjusting position, wherein the sealing piece adjusting apparatus comprises:

a pull wire; and a pull wire channel, wherein a distal end of the pull wire is connected to the sealing piece; the pull wire penetrates through the pull wire channel, wherein the pull wire is capable of being controlled to move along the pull wire channel, to drive the sealing piece to be switched between the first adjusting position and the second adjusting position, wherein the guiding piece is connected to a proximal end of the pull wire, and the guiding piece is capable of being controlled to drive the pull wire to move along the pull wire channel, to drive the sealing piece to be switched between the first adjusting position and the second adjusting position.

* * * * *